United States Patent [19]
Soga et al.

[11] Patent Number: 5,364,381
[45] Date of Patent: Nov. 15, 1994

[54] AIR-PERMEABLE AND LIQUID-IMPERMEABLE BACKSHEET FOR USE IN BODY FLUID ABSORBENT ARTICLES, AND ITS MANUFACTURING METHOD

[75] Inventors: Hiroyuki Soga, Kawanoe; Michiyo Matsushita, Iyomishima, both of Japan

[73] Assignee: Uni-Charm Corporation, Ehime, Japan

[21] Appl. No.: 8,364

[22] Filed: Jan. 22, 1993

[30] Foreign Application Priority Data

Jan. 28, 1992 [JP] Japan .................. 4-038829

[51] Int. Cl.$^5$ .................. A61F 13/15; A61F 13/20
[52] U.S. Cl. .................. 604/366; 604/358; 604/370; 604/367; 604/382
[58] Field of Search .............. 604/358, 366, 367, 369, 604/370, 384, 382; 602/58-59

[56] References Cited

U.S. PATENT DOCUMENTS

| | | |
|---|---|---|
| 3,640,829 | 2/1972 | Elton et al. |
| 3,870,593 | 3/1975 | Elton et al. |
| 4,308,303 | 12/1981 | Mastroianni et al. |
| 4,629,643 | 12/1986 | Curro et al. .................. 604/385.1 |
| 5,073,316 | 12/1991 | Bizen et al. |
| 5,078,708 | 1/1992 | Haque . |

FOREIGN PATENT DOCUMENTS

| | | |
|---|---|---|
| 0232060 | 8/1987 | European Pat. Off. |
| 0319222 | 6/1989 | European Pat. Off. |
| 2115702 | 9/1983 | United Kingdom . |

OTHER PUBLICATIONS

Database WPIL, Section Ch, Week 8818, 24 Mar. 1988–Derwent Publications–London Class A08 AN 88-122681 JP-A-63 066 241 (Dainippon Printing KK).
Database WPIL, Section Ch, Week 8809, 25 Jan. 1988 Derwent Publications London Class A04 AN-88061346 JP-63 017 941 Nitto Electric Ind kk.
Database WPIL Section Ch, Week 9112, Feb. 1991 Derwent Publications London Class A04 AN-9-1-084439 JPA-3 030 934 UniCharm KK.

Primary Examiner—Randall L. Green
Assistant Examiner—P. Zuttarelli
Attorney, Agent, or Firm—Fred Philpitt

[57] ABSTRACT

Here is disclosed air-permeable and liquid-impermeable backsheet for use in body fluid absorbent articles.

Polyolefin plastic sheet containing inorganic filler particles is stretched and then thermo-embossed to obtain the backsheet 1. At least one surface of this backsheet 1 is composed of a rough surface zone 5 and a smooth surface zone 6 so that these two kinds of zones define together a desired surface pattern over the backsheet. The rough surface zone 5 has fine pores 7 for air-permeability and the smooth surface zone 6 facilitates an absorbent core of the body fluid absorbent article to be seen through this smooth surface zone 6.

1 Claim, 3 Drawing Sheets

FIG.I
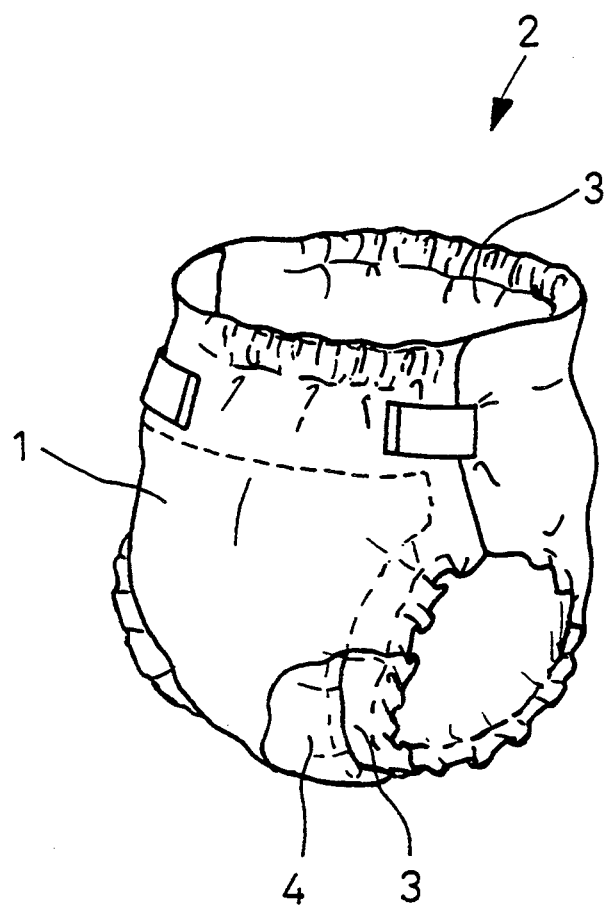

AIR-PERMEABLE AND LIQUID-IMPERMEABLE BACKSHEET FOR USE IN BODY FLUID ABSORBENT ARTICLES, AND ITS MANUFACTURING METHOD

BACKGROUND OF THE INVENTION

This invention relates to air-permeable and fluid-impermeable backsheets made of polyolefin plastic sheet for use in body fluid absorbent articles such as disposable diapers, sanitary napkins and the like.

It is well known to use a polyolefin plastic sheet such as a polyethylene sheet as liquid-impermeable sheet which covers absorbent cores of body fluid absorbent articles. Use of a polyethylene sheet, which is made transparent or translucent, allows the absorbent cores stained with body fluid to be identified through observation of the sheet, and such a sheet is convenient for judgement of the time at which the body fluid absorbent articles thus stained with body fluids should be exchanged with fresh ones. However, such a well known sheet is relatively poor in its air-permeability and therefore the body fluid absorbent articles employing such a backsheet tend to become stuffy. It is also well known to stretch polyolefin plastic sheet such as a polyethylene sheet containing fine particles of inorganic filler, such as calcium carbonate, at a desired draw ratio in order to form air-permeable fine pores and to use such sheet as an air-permeable and liquid-impermeable backsheet as disclosed, for example, in Japanese Patent Application Disclosure Gazettes Nos. 1985-199037 and 1987-167332. These conventional techniques are certainly convenient in preventing the body fluid absorbent articles from becoming stuffy during use thereof owing to improved air-permeability. However, while such a sheet of prior art exhibits a certain transparency before stretching treatment, once it has been stretched, the filler particles are apt to rise to the surface and to form fine projections which, in turn, roughen the sheet surface and thereby increase its optical diffusivity. Consequently, the transparency of the sheet is lost, making it difficult for users to identify that an absorbent core has been stained with body fluids.

To solve these problems, it is a principal object of this invention to provide a backsheet having desired transparency as well as desired air-permeability and being suitable to be used as components of body fluid absorbent articles by subjecting air-permeable polyolefin plastic sheet containing inorganic filler particles and having its surface once roughed by stretching to a thermo-embossing treatment so as to provide partially transparent and smooth surface.

SUMMARY OF THE INVENTION

The object set forth above is achieved, according to one aspect of the invention, by a process for making an air-permeable and liquid-impermeable backsheet for use in body fluid absorbent articles, said process comprising the steps of subjecting polyolefin plastic sheet, containing inorganic filler particles of 30 to 80% by weight, to a pore formation treatment at least including a step of stretching not only in order to form this sheet with air-permeable fine pores but also in order to roughen at least one surface of said sheet and thereafter thermo-embossing said sheet so that said roughed surface is partially smoothed in contrast with the remaining rough surface.

The object set forth above is achieved, according to another aspect of the invention, by an air-permeable but liquid-impermeable backsheet for use in body fluid absorbent articles, said backsheet comprising a polyolefin plastic sheet containing inorganic filler particles of 30 to 80% by weight, at least one surface of said sheet being composed of a rough surface zone having a large number of fine projections formed by the rising up of said particles as well as a large number of air-permeable fine pores and a smooth surface zone in contrast with the remaining rough surface zone.

Preferably, said rough surface zone and said smooth surface zones define together a desired surface pattern.

According to this invention, the air-permeable and liquid-impermeable backsheet is made by stretching the polyolefin plastic sheet containing inorganic filler particles so that the sheet surface may be roughed by the filler particles rising up to the surface as air-permeable fine pores are formed. This surface roughed sheet is thermo-embossed, by which part(s) the sheet coming into contact with an embossing roll is softened or become molten under pressure and the rough surface is converted to a smooth surface. The embossing roll may be provided with a desired pattern to obtain a corresponding sheet surface pattern composed of the smooth surface zone and the rough surface zone. Use of this sheet carrying thereon such surface pattern as the backsheet serving to cover the absorbent core of the body fluid absorbent articles facilitates identification of the absorbent core stained with body fluids since the smooth surface zone has an adequate transparency, on the one hand, and allows the absorbent core stained with body fluids to be effectively concealed by the rough surface zone since the rough surface zone has a poor transparency due to optical diffusion and thereby said identification is made difficult, on the other hand. Even after being thermo-embossed, such sheet maintains the air-permeable fine pores at least over the rough surface zone.

BRIEF DESCRIPTION OF THE DRAWINGS

The invention will be described more in detail with reference to the attached drawings, in which:

FIG. 1 is a perspective view of a disposable diaper using the backsheet of the invention;

PREFERRED EMBODIMENTS OF THE INVENTION

Figure 2A:
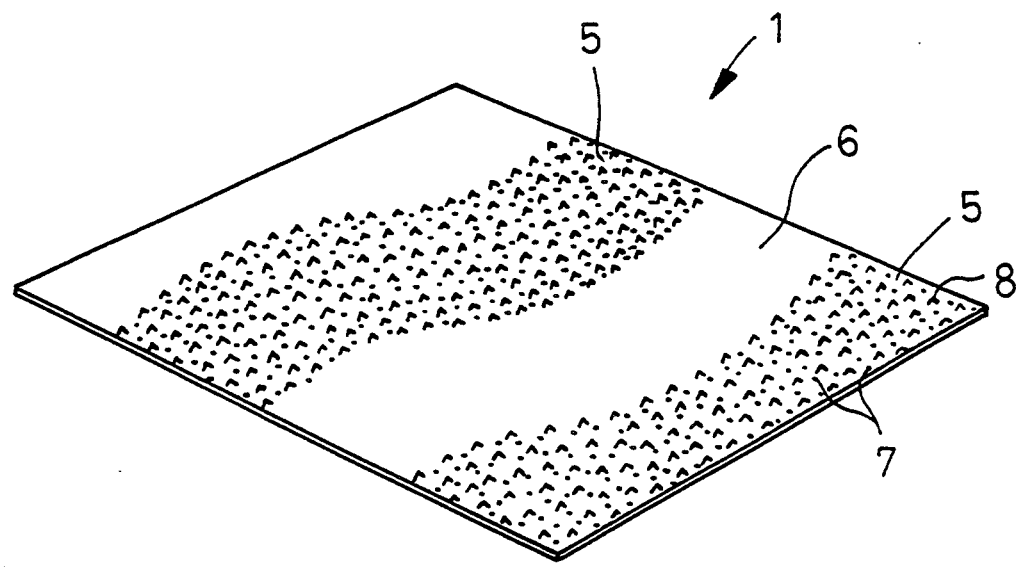
FIG. 2 is a fragmentary enlarged view showing examples (a) and (b) of the surface pattern.

FIG. 1 is a perspective view showing, as partially broken away, disposable diaper 2 positioned so as to be ready for actual use, said diaper 2 including a the surface-patterned air-permeable backsheet 1 of the invention. As on the prior art, the diaper 2 basically comprises a topsheet 3, the backsheet 1 and an absorbent core 4 sandwiched between these sheets 1, 3. The backsheet 1 defines the outer side of the diaper 2 and has sufficient liquid impermeability to prevent body fluid from leaking.

FIG. 2 is a fragmentary perspective view showing, in an enlarged scale, the backsheet 1 of the invention, with (a) and (b) illustrating two examples of the backsheet having different surface patterns. The backsheet 1 is a polyethylene sheet having a thickness of 50 μm and containing particles of inorganic filler such as calcium carbonate or barium sulfate of 30 to 80% by weight.

Figure 2B:
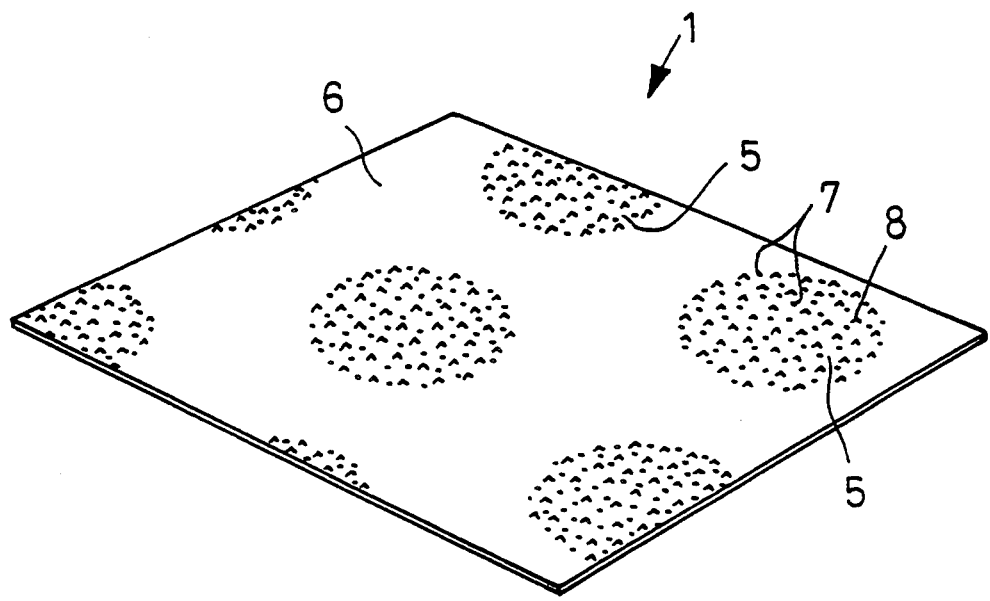

At least one surface of the backsheet 1 comprises a rough surface zone 5 and a relatively smooth surface zone 6 so that these two zones represent, for example, a striped pattern as shown by FIG. 2A or polka dots as shown by FIG. 2B. The rough surface zone 5 includes a large number of fine pores 7 each having a diameter of 0.03 to 5 μm and a large number of fine projections 8 formed by the rising up of the filler particles. Presence of the fine pores 7 makes the rough surface zone 5 air-permeable but practically maintains liquid-impermeability of this zone 5 while the presence of the fine projections 8 causes whitening of this zone 5 due to optical diffusion of transmitted light and reflected light. On the other hand, the smooth surface zone 6 includes thereon practically none of the fine projections 8 or, if any, they will be substantially lower in number than the fine projections 8 on the rough surface zone 5 so that the optical diffusion of both transmitted light and reflected lighted may be reduced and thereby it may be assured to obtain a transparency higher than that of the rough surface zone 5. The smooth surface zone 6 may or may not have the fine pores 7.

With the backsheet 1 being in the state for actual use as shown by FIG. 1, occurrence of excretion can be readily identified and thereby an opportunity to exchange the diaper 2 can be judged, since the absorbent core stained with body fluids can be seen through the smooth surface zone 6. On the other hand, it is the relatively difficult for the stained absorbent core to be seen through the rough surface zone 5 and, therefore, this rough surface zone 5 can be used to conceal the stained absorbent core 4. For this purpose, the location as well as size of the rough surface zone 5 may be appropriately selected. Respective configurations of the rough surface zone 5 and the smooth surface zone 6 as well as ratio of their areas may be also appropriately selected to obtain a desired surface pattern on the backsheet 1. It should be understood that FIG. 2 illustrates both the fine pores 7 and the fine projections 8 in exaggerated sizes relative to the thickness of the backsheet 1 to clarify the presence of them.

Figure 3:
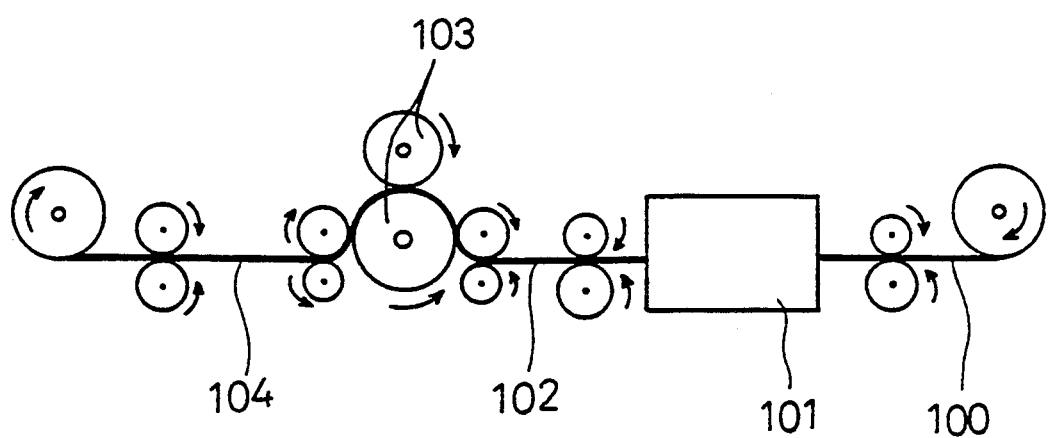
FIG. 3 is a schematic diagram illustrating a process for making the backsheet.

FIG. 3 is a schematic diagram illustrating a process of making the backsheet 1. Polyethylene sheet 100 having a thickness of approximately 20 μm which contains particles of inorganic filler such as calcium carbonate or barium sulfate of 30 to 80% by weight is fed to a tenter 101 by which the sheet 100 is stretched both in length and width by 100% under heating condition, and then cooled to obtain stretched sheet 102 having the air-permeable fine pores 7 and the opposite surfaces roughed. The stretched sheet 102 is passed between a pair of embossing rolls 103 comprising a combination of a pattern roll having thereon the striped pattern as shown by FIG. 2A and a smooth surface roll whereby the roughed surfaces are partially smoothed by heating them under a sufficient pressure so as to obtain air-permeable sheet 104 having the surface pattern defined by the rough surface zone and the smooth surface zone. Then, this sheet 104 is appropriately cut to obtain individual backsheets 1.

When used particularly for a disposable diaper, the backsheet 1 preferably has a thickness of 20 to 80 μm. Content of the inorganic filler particles in the backsheet 1 may be selectively adjusted to achieve the desired air-permeability and transparency, i.e., see-through characteristic.

The backsheet 1 of this invention is air-permeable through the fine pores provided over the rough surface zone which is also effective to cover up the absorbent core stained with body fluids excreted and absorbed therein and thereby to keep the body fluid absorbent articles in an acceptable appearance. The smooth surface zone allows users to judge an opportunity to exchange the stained body fluid absorbent articles with fresh ones, since the smooth surface zone has a see-through characteristic which facilitates identification of the stained absorbent core. The rough and smooth surface zones may be appropriately arranged to represent a desired surface pattern over the backsheet. Such backsheet can be easily made by stretching polyolefin plastic sheet which contains the inorganic filler particles and subsequently thermo-embossing such stretched sheet.

What is claimed is:

1. An article for absorbing body fluid comprising a layer of absorbent material and a backsheet that is liquid-impermeable, the improvement comprising
   (1) said backsheet being composed of a stretched polyolefin plastic containing 30 to 80% by weight of embedded inorganic filler particles based on the weight of the backsheet,
   (2) said backheet contains at least one roughened portion that includes a large number of air-permeable fine pores and a large number of fine projections rising upwardly and formed from the rising up of said filler particles when the backsheet is stretched, and
   (3) the remainder of said backsheet being composed of a smooth thermo-embossed surface containing air-permeable fine pores that is substantially free of fine projections which rise up and which thermo-embossed surface has a higher transparency than said at least one roughened portion.

* * * * *